United States Patent

Ocleppo

[11] Patent Number: 6,005,912
[45] Date of Patent: Dec. 21, 1999

[54] NON-DESTRUCTIVE X-RAY INSPECTION APPARATUS FOR FOOD INDUSTRY

[75] Inventor: Rinaldo Ocleppo, Canale, Italy

[73] Assignee: Dylog, Italia, S.p.A., Turin, Italy

[21] Appl. No.: 09/047,130

[22] Filed: Mar. 24, 1998

Related U.S. Application Data

[63] Continuation-in-part of application No. 08/804,425, Feb. 21, 1997, abandoned.

[51] Int. Cl.⁶ ..................................................... G01N 23/04
[52] U.S. Cl. ................................................. 378/57; 378/58
[58] Field of Search ......................................... 378/57, 58

[56] References Cited

U.S. PATENT DOCUMENTS

| | | | |
|---|---|---|---|
| 3,958,078 | 5/1976 | Fowler et al. | 178/6.8 |
| 4,064,440 | 12/1977 | Roder | 378/57 |
| 4,566,113 | 1/1986 | Donges et al. | 378/57 |

*Primary Examiner*—Craig E. Church
*Attorney, Agent, or Firm*—Paul & Paul

[57] ABSTRACT

Inspection apparatus for product-containing glass vessels and/or cans for the food industry, having a static structure including two modular units mutually placed at 90° in relation to each other and placed at 45° with respect to a line of vessels being conveyed by the apparatus, one unit being equipped with a semi-panoramic emitter and a sensor, the other unit being equipped only with a sensor, equal to the sensor of the first unit. With this inspection structure with a single emitter and two sensors a 100% inspection is realized.

16 Claims, 3 Drawing Sheets

NON-DESTRUCTIVE X-RAY INSPECTION APPARATUS FOR FOOD INDUSTRY

CROSS-REFERENCE TO RELATED APPLICATIONS

This is a continuation-in-part of U.S. application Ser. No. 08/804,425, filed Feb. 21, 1997, which claims foreign priority from Italian Application No.: TO96A000203 filed Mar. 15, 1996.

BACKGROUND OF THE INVENTION

1. Field of Invention

The present invention relates to a non-destructive X-ray inspection apparatus for the food industry, particularly for glass vessels and/or metal cans.

2. Brief Description of the Prior Art

It is known that, in the vast majority of cases, non-destructive X-ray inspection of glass vessels in food industry applications is carried out by single devices, located on one side of the row of said vessels to be inspected; said devices being substantially equipped with an emitter and a sensor between which the row of said vessels to be inspected moves.

Similarly known is the fact that with such single devices a 90–95% inspection is obtained of the product contained therein, said deficiency being due to the shadow area projected by the concavity that is present, more or less importantly, in the vessel bottom.

To be more precise, refer to a glass vessel containing jam or a similar product; the impairing concavity is the one on the bottom of these vessels; this projection overlaps the contaminating agents hiding them and making their recognition impossible.

In many cases this result has been deemed, wrongly, enough, because an inspection valid only at 95% created a lot of problems, which it was attempted to solve through a few solutions, that proved, however, rather complicated and costly and not satisfactory enough.

Among the above solutions, mention can be made of a 45° slant on the vertical emitter pipe plan. This solution, however, only generated another shadow area in another point with respect to the traditional inspection apparatus placed on one side. Moreover, though mitigating the darkening, it did not solve the problem (which is often due to high vessel tolerances). Furthermore, it cannot be applied to cans.

Another solution being studied in the United Kingdom provides two inspection apparatus mutually placed at 90° on the vertical plan.

This latter solution seems to benefit from a partial reduction of shadow areas, but it uses two inspection apparatus and the system overall dimensions are rather big; the cost for the two apparatus, their maintenance and the like are important cost elements that cannot be overlooked.

Other prior attempts to deal with the problems associated with inspection of contents include arrangements where the X-ray radiation from a source is altered or intensified, before being detected. The intensification of X-ray radiation, however, can bring about image distortion in the upper portion of a jar. An X-ray inspection technique has been used in U.S. Pat. No. 3,958,078 "X-Ray Inspection Method and Apparatus" which employs a brightness intensifier to modify X-ray radiation which is then viewed by a camera.

Another U.S. Pat. No. 4,064,440 "X-Ray or Gamma Ray Examination Device for Moving Objects" employs a bank of adjacent detectors arranged in an array. The "Method and Apparatus for Examining the Content of Containers" disclosed in U.S. Pat. No. 4,566,113 provides a method for ascertaining the weight of container contents with an X-Ray technique. A "Measuring and Controlling System" which uses X-Ray radiation for controlling the height of material deposited into a container by an automatic dispensing machine is disclosed in U.S. Pat. No. 3,007,048.

A need still exists for a solution which is economical and accurately able to inspect vessels with the problem of the shadowed or hidden areas being addressed.

SUMMARY OF THE INVENTION

An object of the present invention is solving the above-mentioned problem of removing the shadow area when inspecting packaged vessels, thus realizing an improved, simple, and practical apparatus that allows easily obtaining the provided objective of a complete inspection of sealed vessels.

The inspection apparatus of the present invention includes a static structure with two modular units mutually placed at 90° with respect to each other, and placed at 45° with respect to a feeding line for vessels to be inspected; a first one of said two units being equipped with a semi-panoramic emitter and an X-Ray linear sensor, a second one of said two units being equipped only with a sensor, equal to said sensor of said first unit; said inspection structure with a single emitter and two sensors comprising a structure which is able to inspect 100% of a product contained in said vessels.

The advantages of the apparatus of the invention are as follows:

modularity: therefore, with the same performance, a starting price (for the single module) is much less than the standard price, thus widening product markets; the apparatus can be provided to comprise modular parts which can be connected to form the apparatus;

with two sensors, a simultaneous failure thereof is statistically impossible, so that a user can go on working even in case one of the two sensors fails (inspecting 95% of the product);

there are practically no installation problems with related costs;

there are no costs for mechanical spare parts, since the structure is substantially static with obvious maintenance advantages;

there are no problems of space, thus complying with the food industry needs whose lines are almost always full and without spaces for apparatus not provided for when designing.

Further features and advantages will appear from the following detailed description of the invention, with reference to the accompanying drawings, provided as a non-limiting example.

BRIEF DESCRIPTION OF THE DRAWING FIGURES

DETAILED DESCRIPTION OF THE INVENTION

Figure 1:
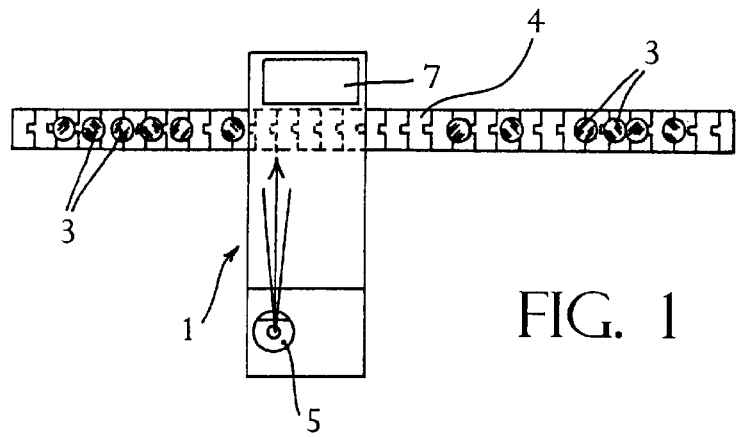
FIG. 1 is a schematic plan view of a prior art inspection apparatus, placed at 90° with respect to the line of vessels to be inspected.
Figure 2:
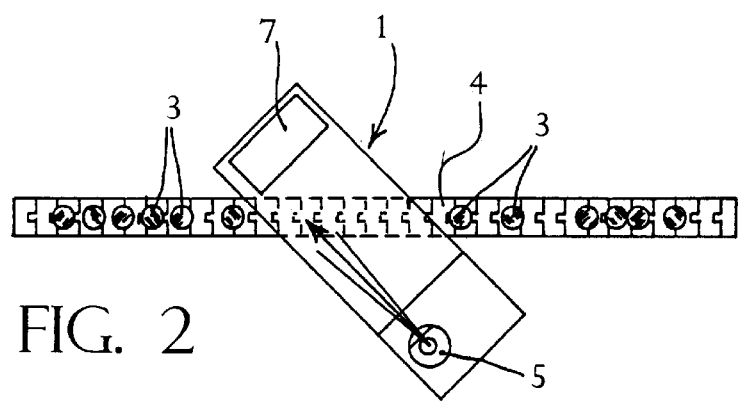
FIG. 2 is a schematic plan view of a prior art inspection apparatus, placed at 45° with respect to the line of vessels.
Figure 3:
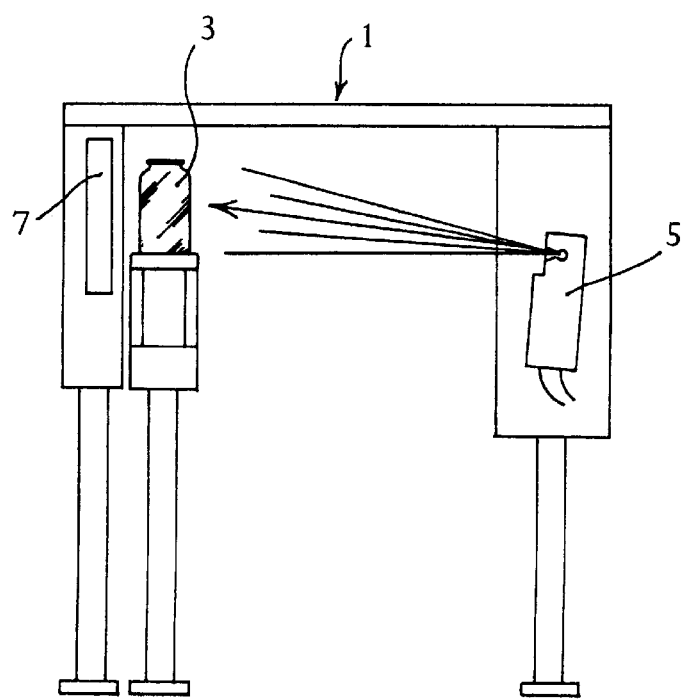
FIG. 3 is a schematic sectional view of the prior art apparatus shown in FIG. 1.

As appears from FIGS. 1 and 3, prior art inspection apparatus are composed of a structure 1 bridging a row of glass vessels 3 to be examined that are moved along thereunder by a conveyor 4.

This structure includes an X-ray emitter 5 and a sensor 7, that collects rays emitted by the emitter 5 and displays what has been inspected. Preferably, the sensor 7 of the present apparatus is a linear sensor wherein the radiation emitted by an emitter 5, 15 is received directly in its unaltered condition by the sensor 7, except to the extent that any radiation is absorbed by the vessel 3 and its contents.

Figure 6:
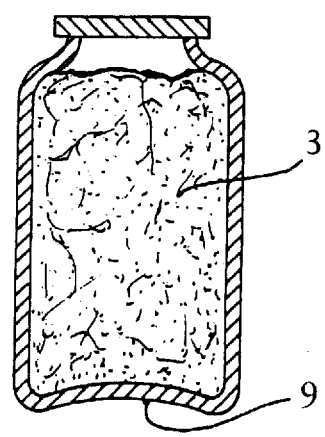
FIG. 6 is a section of a glass vessel with the typical bottom concavity.

If a glass vessel is taken into account (see FIG. 6), it can be clearly seen how the concavity 9 provided on the bottom of said vessel 3 impairs a complete inspection of the product in the vessel 3; should this concavity or internal projection 9 be missing, obviously there would be no problems.

Figure 4:
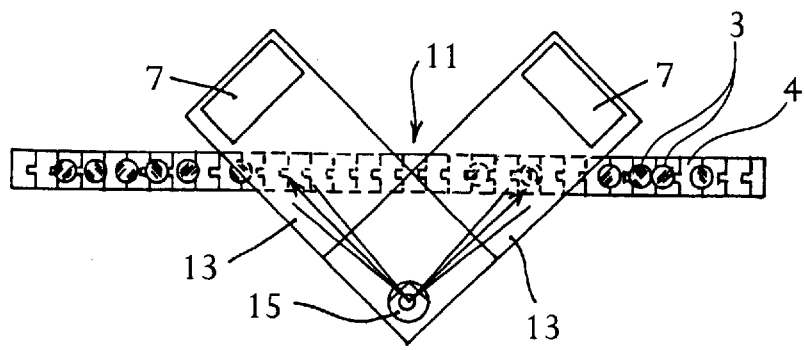
FIG. 4 is a schematic plan view of an inspection apparatus according to a first embodiment of the invention.

With the inspection apparatus of the invention shown in FIG. 4, instead, a static structure 11 is provided, comprised of two modular units 13 placed at 90° in relation to each other and at 45° with respect to the feeding line of vessels 3 to be inspected.

One of these two units 13 is equipped with a semi-panoramic emitter 15 and with a normal sensor 7, while the other unit is equipped only with the sensor 7 equal to the one in the first unit.

Figure 5:
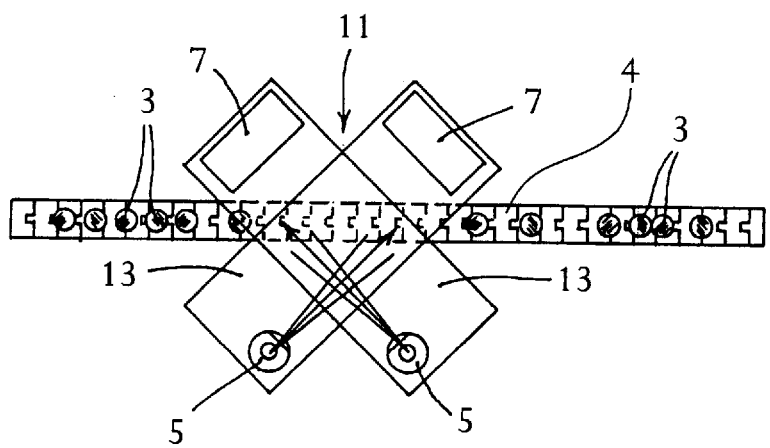
FIG. 5 is a schematic plan view of an inspection apparatus according to a second embodiment of the invention.

In the embodiment of the inspection apparatus shown in FIG. 5, both units 13 are each equipped with a standard emitter 5 and a sensor 7. The emitter 5 provides an X-ray emission of radiation to the linear sensor 7.

It is clear that in this way shadow areas created by the concavity 9 (FIG. 6) of the vessels 3 to be inspected, are removed, since the area not detected by a sensor will be detected by the other sensor at 90° with respect to the first one.

It is clear that, in case of failure of one of these sensors 7, a user can go on working, if he deems it adequate, with only one of them, always getting a 95% inspection as was the case in prior art.

The modular units 13 of the present apparatus 11 can further be provided so that each of the modular units 13 is adapted to hold an emitter and a sensor. Attachment means can be provided for attaching an emitter and a sensor to a modular unit 13. Each modular unit can contain means for selectively mounting an emitter and a sensor thereon. With this configuration, the modular units can be adapted to contain a sensor and an emitter. For example, the semi-panoramic emitter 15 can be installed in one of the modular units 13, or the standard emitter 5 can be installed in each of the modular units 13. Similarly, the units 13 can be provided with an emitter, such as the standard emitter 5 or semi-panoramic emitter 7, and sensor 7, installed thereon.

Figure 7:
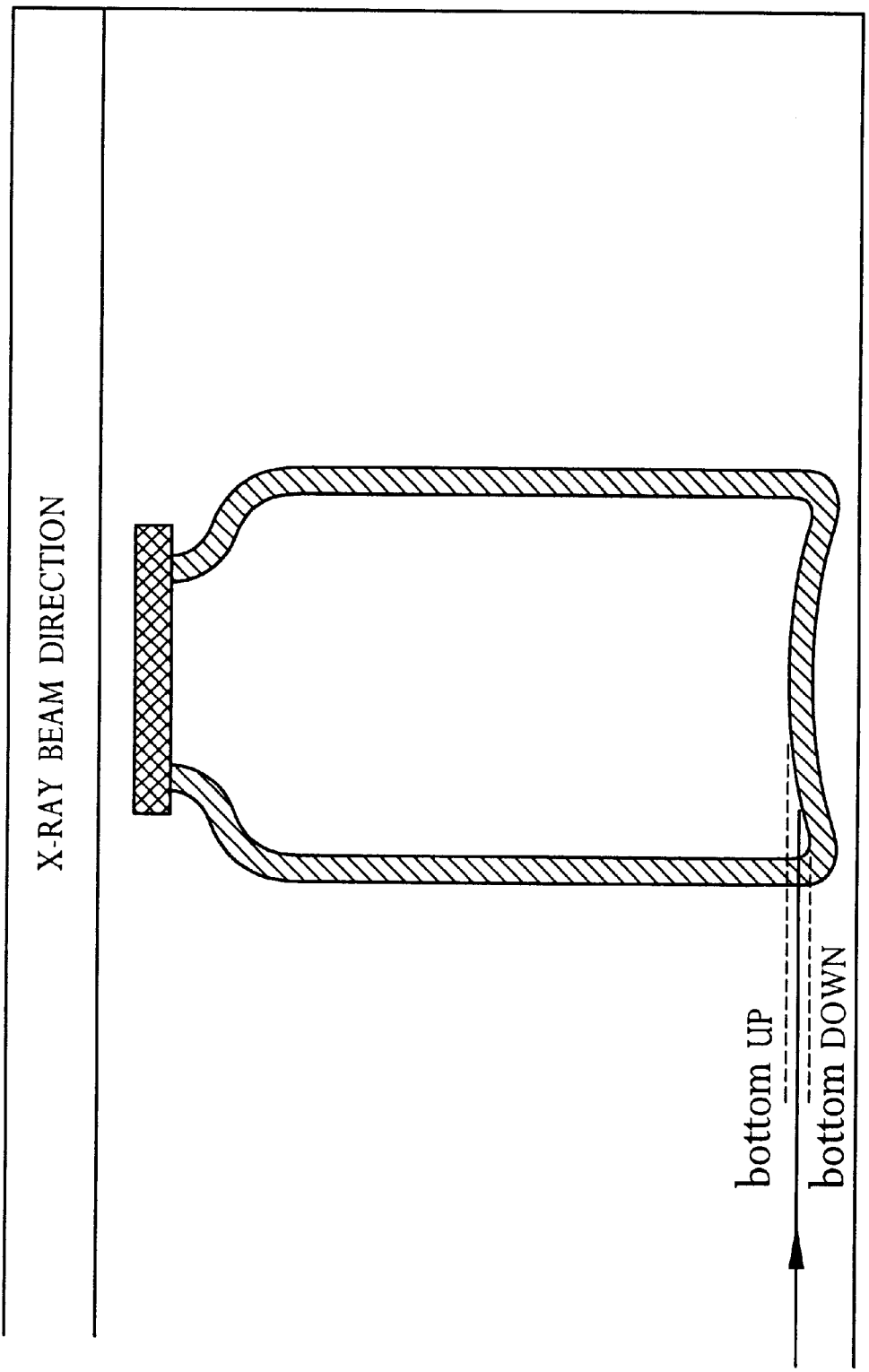
FIG. 7 is an enlarged view of a glass vessel shown on a conveyor of the apparatus with the X-ray direction indicated.

FIG. 7 shows a vessel according to the present invention with the path of X-ray travel being identified by the arrow. This figure shows the orientation of the vessel 3, with respect to the plane of emission of the x-rays. The vessel 3 is provided in a vertical orientation in relation to the conveyor or other traveling means shown in FIGS. 4 and 5. The X-ray radiation is emitted and measured in the horizontal plane with respect to the vertically positioned vessel 3. The vessels 3 are conveyed along the same path of travel such that each next vessel 9 in the feed line of vessels travels through the same location with respect to the modules 13.

In the present apparatus, signals are generated by each sensor 7. The arrangement of the two linear sensors 7 permits the processing of the two signals generated to be carried out in a parallel manner. The parallel processing of the two signals does not require the comparison of images or data. The speed of processing which can be carried out for the signals from the sensors is therefore increased. Furthermore, the processing speed can be further increased by using two identical processors (not shown). An algorithm will be installed on, or embedded in, the processor, which will process the signals from the sensors and feed the results to a single discriminating unit (not shown). The results are then used by the discriminating unit to actuate a mechanism, alarm, or other feature, which will enable the removal of the suspicious vessel from the feed line.

As described above, the present invention preferably is provided having a modular configuration. For example, a first unit 13 can be supplied with an emitter 5 and a sensor 7, to be used with a second unit 13 identical thereto except without the emitter. The emitter 5 can also be modularly provided, for example, to be received on a unit. In this manner, the units can be purchased, the emitter and the sensors, each as separate components which are installed to operate in the manner described herein.

Although the present invention has been described with reference to preferred embodiments, numerous modifications and rearrangements can be made and still the result will come within the scope of the invention.

I claim:

1. A non destructive X-ray inspection apparatus for inspecting product-containing articles including glass vessels and/or cans for food industry, the apparatus comprising:

a) transport means for transporting said articles through a substantially straight feeding line through said apparatus;

b) a first unit having emitter means for emission of X-ray beams therefrom and sensor means for collecting said X-ray beams emitted from said emitter means and generating a first signal from said first sensor means;

c) a second unit having sensor means for collecting said X-ray beams emitted from said emitter means and generating a second signal from said second sensor;

d) wherein said first and second units are placed in relation to each other in such a manner that X-ray beams collected by said sensor means in said first unit and X-ray beams collected by said sensor means in said second unit form an angle of 90 degrees in relation to each other, and wherein said first and second units are placed in relation to said transport means in such a manner that X-ray beams collected by said sensor means in said first unit intersects said feeding line at an angle of 45 degrees;

e) wherein said sensor means includes a pair of matched sensors;

f) one each of said sensors being provided in said first unit and in said second unit;

g) wherein said first signal and said second signal are processed in a parallel manner;

h) wherein said first signal is processed separately and simultaneously in relation to said second signal.

2. The apparatus according to claim 1, wherein each one of said two units is equipped with a standard emitter and a sensor.

3. The apparatus according to claim 2, wherein said apparatus can be used as a normal unitary structure for a 95% inspection using a single one of said first unit and said second unit at 45° with respect to the line of vessels to be examined, using said emitter and only one of said pair of matched sensors.

4. The apparatus of claim 1, wherein said apparatus with a single emitter and two sensors provides the capability to inspect 100% of a product contained in said articles.

5. The apparatus of claim 1, wherein said emitter means comprises a semi-panoramic emitter.

6. The apparatus of claim 1, wherein said emitter means comprises a standard emitter, and wherein said first unit and said second unit each contain a standard emitter.

7. The apparatus of claim 1, wherein said first and second units are adapted to hold emitter means and a sensor.

8. The apparatus of claim 7, wherein said first unit includes mounting means for said selectively mounting emitter means and a sensor thereon, and wherein said second unit includes mounting means for selectively mounting emitter means and a sensor thereon.

9. The apparatus of claim 1, further including processor means, wherein said sensors each provide an output to said processor means and wherein said output received by said processor means is received and processed simultaneously.

10. The apparatus of claim 9, wherein said processor means includes a pair of matched processors.

11. The apparatus of claim 9, wherein said apparatus further includes discriminating means, said discriminating means being selectively actuated by said processor means, wherein said discriminating means includes alerting means for alerting of the presence of suspicious contents of said article.

12. The apparatus of claim 9, wherein said apparatus further includes discriminating means, said discriminating means being selectively actuated by said processor means, wherein said discriminating means further includes engaging means for selectively engaging a suspect article being conveyed and removing said suspect article from said conveyor.

13. The apparatus of claim 1, wherein said articles are transported vertically with said transport means.

14. The apparatus of claim 1, wherein said transport means comprises conveyor means.

15. The apparatus of claim 1, further comprising a conveyor for moving articles through said apparatus.

16. The apparatus of claim 15, wherein said articles are transported vertically with said conveyor.

* * * * *